United States Patent
Effenhauser et al.

(10) Patent No.: US 7,527,740 B2
(45) Date of Patent: May 5, 2009

(54) METHOD AND SEPARATING MODULE FOR THE SEPARATION OF PARTICLES FROM A DISPERSION, IN PARTICULAR OF BLOOD CORPUSCLES FROM BLOOD

(75) Inventors: Carlo Effenhauser, Weinheim (DE); Gregor Ocvirk, Mannheim (DE); Wolfgang Fiedler, Laudenbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 524 days.

(21) Appl. No.: 10/492,256

(22) PCT Filed: Sep. 14, 2002

(86) PCT No.: PCT/EP02/10336
§ 371 (c)(1),
(2), (4) Date: Oct. 7, 2004

(87) PCT Pub. No.: WO03/033096
PCT Pub. Date: Apr. 24, 2003

(65) Prior Publication Data
US 2005/0029190 A1    Feb. 10, 2005

(30) Foreign Application Priority Data
Oct. 12, 2001 (DE) .............................. 101 50 549

(51) Int. Cl.
*B01D 37/00* (2006.01)
*B01D 11/00* (2006.01)

(52) U.S. Cl. .......................... 210/806; 210/767; 435/2; 436/177

(58) Field of Classification Search ................. 210/199, 210/201, 209, 252, 321.6, 321.75, 321.84, 210/335, 336, 337, 644, 767, 806; 422/99, 422/101; 436/43, 177; 435/2
See application file for complete search history.

(56) References Cited

U.S. PATENT DOCUMENTS 3,791,933 A    2/1974   Moyer et al. ................. 195/127

(Continued)

FOREIGN PATENT DOCUMENTS
EP         0 057 907         8/1982

(Continued)

OTHER PUBLICATIONS

Pries, A.R., Secomb, T.W., Gaehtgens, P., "Biophysical aspects of blood flow in the microvasculature", Cardiovascular Research 32 (1996) 654-667.

*Primary Examiner*—John Kim
(74) *Attorney, Agent, or Firm*—Barnes & Thornburg LLP

(57) ABSTRACT

A method for separating particles from a fluid dispersion, particularly for separating corpuscular components from biological samples, above all from blood. A separating module suitable for performing the method has a substrate with flow channels, comprising a feed channel for supplying the dispersion to a junction, a first drain channel for draining fluid having a reduced particle concentration away from the junction, and a second drain channel for draining fluid having an increased particle concentration away from the junction. The fluid flows so much faster in the second drain channel than in the first drain channel that due to the different flow speeds the dispersed particles preferentially flow at the junction further in the second drain channel.

5 Claims, 4 Drawing Sheets

U.S. PATENT DOCUMENTS

| | | | |
|---|---|---|---|
| 4,477,575 A | 10/1984 | Vogel et al. | 436/170 |
| 5,922,210 A | 7/1999 | Brody et al. | 210/767 |
| 6,045,699 A | 4/2000 | Yazawa et al. | 210/637 |
| 6,676,835 B2* | 1/2004 | O'Connor et al. | 210/542 |
| 6,935,772 B2* | 8/2005 | Karp et al. | 366/341 |
| 2002/0037499 A1* | 3/2002 | Quake et al. | 435/5 |
| 2002/0187072 A1* | 12/2002 | Karp | 422/60 |
| 2003/0036206 A1* | 2/2003 | Chien et al. | 436/180 |
| 2004/0037739 A1* | 2/2004 | McNeely et al. | 422/58 |

FOREIGN PATENT DOCUMENTS

| | | |
|---|---|---|
| JP | 60201253 | 10/1985 |
| WO | PCT/US98/16870 | 2/1999 |

\* cited by examiner

METHOD AND SEPARATING MODULE FOR THE SEPARATION OF PARTICLES FROM A DISPERSION, IN PARTICULAR OF BLOOD CORPUSCLES FROM BLOOD

PRIORITY CLAIM

This application claims priority to PCT Application Number PCT/EP02/10336 filed Sep. 14, 2002, which is based on German Application Number DE 101 50 549.3 filed Oct. 12, 2001.

TECHNICAL FIELD

The invention relates to a method for separating particles from a dispersion and a component for performing such a method. Since such a component may be used modularly as part of different systems, it is referred to here as a separating module. The invention may particularly be used for separating corpuscular components from biological samples, above all from blood.

BACKGROUND

The problem of partially or completely removing the particles from a dispersion which contains particles dispersed in a carrier medium occurs in various fields of application. An especially important field is analytical methods for determining the concentration of components in blood. Such blood tests may in many cases not be performed with whole blood which contains the corpuscular components (blood corpuscles). Rather, it is necessary to obtain, from the whole blood, plasma which is as free as possible from cellular material.

The invention is, however, also suitable for treating other dispersions. The carrier medium must not be liquid, but rather can also be gaseous. An example of the application of the invention in the framework of diagnostic-analytic methods, in which a non-biological liquid is treated, is the manipulation, enrichment, or isolation of microbeads which, because of their large renewable surface, have recently been increasingly used in combinational chemistry and molecular biology, for example. In addition, the invention may also be used in other fields of chemical process engineering and the food industry in order to separate particles from process streams. Further usage possibilities exist in biotechnological methods (removal and isolation of cell cultures from corresponding dispersions) and in the field of wastewater purification. Without restriction of the generality, reference will be made hereafter to the treatment of dispersions in liquids, mainly the separation of plasma from whole blood.

Traditionally, centrifugation methods have been used in order to obtain for blood tests plasma by separation of the cellular components. However, this is not suitable for modern miniaturized tests. This is particularly true for point-of-care testing in which an analysis element (in the form of a test strip, for example) that is as small and compact as possible contains all of the reagents and other agents necessary for performing the test, so that the sample liquid must only be brought into contact with the analysis element in order to determine the desired analytical result visually or with the aid of an analysis instrument on the basis of a physical change detectable on the analysis element (particularly a color change or a change of an electrical measurement variable).

In order to obtain plasma for tests of this type from relatively small blood volumes, filtration methods have been discussed and used with some success for many years. Different filter media, particularly microporous membranes and fiberglass matting, are used. Early examples of these filtration technologies are described in U.S. Pat. Nos. 3,791,933 and 4,477,575. A more recent example having a complex combination of membrane and fiberglass filters is the subject of U.S. Pat. No. 6,045,699.

In U.S. Pat. No. 5,922,210 a microcomponent is described which is to be used for the purpose of obtaining by microfiltration extremely small quantities of plasma in the range up to approximately 1 µl. In a silicon substrate microchannels are generated by etching. The separation of the blood corpuscles is achieved by a barrier channel having a depth of less than 0.1 µm, so that the blood corpuscles cannot flow through the barrier channel. The required feed channels and the barrier channel are produced in two sequential production steps. The extremely low depth of the barrier channel of less than 0.1 µm is determined by the duration of the etching procedure in an etching bath. In consideration of the required high reproducibility this production method is very difficult and complex.

The above-mentioned methods for obtaining plasma have significant disadvantages. Above all, there is a high risk that the fine pores are clogged due to mechanical wear or the adhesion of cellular material to the pore walls. The filter capacity is thus limited.

A larger capacity requires a larger space for the filter media. In addition, the relation between the sample volume applied and the plasma volume obtained is unfavorable. Finally, measurement errors may be caused by adhesion of proteins to the filter medium or by the high shear forces during the passage of erythrocytes through the narrow filter pores and by hemolysis resulting therefrom.

On this basis, it is an object of the invention to allow separation of particles from a dispersion, while avoiding, as far as possible, the disadvantages described above, using a separating module which may be produced easily and cost-effectively. The separating module is preferably a "disposable", intended for single use, and should in particular be suitable for generating small amounts of plasma (less than 10 µl, in particular less than 5 µl) for miniaturized tests.

The object is achieved by a method for separating particles from a fluid dispersion, particularly for separating corpuscular components from biological samples, above all from blood, by means of a separating module comprising a substrate with flow channels, including a feed channel for supplying the dispersion to a junction, a first drain channel for draining fluid having a reduced particle concentration away from the junction, and a second drain channel for draining fluid having an increased particle concentration away from the junction, wherein the fluid flows so much faster in the second drain channel than in the first drain channel that due to the different flow speeds the dispersed particles at the junction preferentially flow further in the second drain channel.

Earlier filtration methods used for the purposes of the invention are based on steric selection, i.e. on the fact that the particles to be separated are held back because the pores of the filter medium are smaller than the diameter of the particles. In order to separate erythrocytes reliably in this way, the pore diameter of the filter medium must be at most 1 µm (particularly because of the easy deformability of the erythrocytes).

In the invention, the selection is based on a completely different principle: differing local particle flow speeds in different flow paths of the liquid flow in the separating module lead to shear stresses which cause the particles to preferentially flow at the junction further in the second drain channel having the higher flow speed. The first flow channel having the lower flow speed contains a reduced particle concentration.

A plurality of important advantages are achieved by the invention:

Since the separation of the particles is not based on steric selection, the smallest dimension of the drain channels may be larger than the particle diameter. For example, the flow channels of a separating module suitable for obtaining plasma from whole blood preferably have a smallest cross-sectional dimension of at least 5 µm and at most 150 µm. Values of less than 100 µm, particularly less than 50 µm, are especially preferred. In this way, there is, in contrast to the previously known filtration methods, practically no risk of clogging of the filter medium. An additional advantage is due to the fact that no fibrous materials must be used, which cause additional clogging risk.

According to the invention, blood (or other dispersions) may be treated continuously over long periods of time. The separating module may therefore be used for continuously obtaining (practically) particle-free filtrates or for continuous particle enrichment from dispersions.

The manufacturing is relatively simple and inexpensive. In comparison to previously known filtration methods, it is not necessary to manufacture and integrate a filter medium into the separating module. In comparison to the microfilter described in U.S. Pat. No. 5,922,210, the manufacturing is significantly simpler because the flow channels integrated into the chip have comparatively large dimensions. Such channel structures may be produced cost-effectively in mass production. An especially suitable method includes production of a master by a photolithographic way. A mold may be obtained from this master, and from this mold product chips may be produced by pressing or injection molding (example: production of CDs). Smaller production lots may be produced by laser ablation.

It is advantageous for the production that the invention does not require structures of differing depths. Preferably, at least both drain channels, especially preferably all flow channels, are equally deep. They may be produced easily in a single work step.

The dead volume in the flow channels of the separating module is very small. The invention therefore allows a sufficiently large volume of plasma to be obtained from a very small sample volume.

The separating module according to the invention can be further miniaturized than a system which contains a filter medium and drain channels, and miniaturization does not reduce the efficiency of the separation or the throughput. This again helps to reduce the cost.

The separating module may be integrated easily into a system, particularly an analysis system. In analytical Microsystems, for example, "planar integration" is possible, i.e. reagents and liquid treatment elements necessary for the analysis can be integrated into the same chip in which the flow channels of the separating module are located. However, conventional coupling to an analysis system via tubing lines having a low dead volume is also possible.

The physical effects upon which the invention is based may be partially explained on the basis of experimental investigations of the flow behavior of blood in the capillary system of the body and theoretical considerations based thereon. The available knowledge is summarized, for example, in a review article by A. R. Pries et al., "Biophysical aspects of blood flow in the microvasculature", Cardiovascular Research 32, 1996, 654-667. The authors report inter alia that, at junctions of the capillary vessels transporting the blood in the body, the hematocrit (content of red blood corpuscles) is typically lower in a daughter vessel having a lower blood flow than in a daughter vessel having a higher blood flow. The statement is made that this phase separation can only insufficiently be described theoretically because of the numerous influencing variables and the dependence of the blood flow on these influencing variables, which is non-linear in multiple aspects. Specifically, the "plasma skimming effect", the "network Fahraeus effect", and the "pathway effect" are discussed as physical principles which determine the phase separation in capillary blood vessels. One of these effects, the network Fahraeus effect, describes the tendency of red blood corpuscles to preferentially follow at a junction the flow path having the higher flow rate (and therefore the higher flow speed).

According to the state of knowledge of the inventors, it is to be assumed that this principle essentially explains the function of the separating module according to the invention. It could not be expected, however, that a nearly complete plasma separation could be achieved in a practically usable manner by easily implementable means. This statement is confirmed by the fact that the basic principles about phase separation at capillary junctions have been known since a long time. For example, experimental in vitro investigations of 1964 and in vivo studies of 1970 are cited in the cited review article.

Another reason why the suitability of this principle for plasma separation was not to be expected is that in the natural capillaries no high degree or even complete separation is observed. In contrast, the functioning of the human body is dependent on a sufficiently high concentration of erythrocytes in even the finest capillaries to provide a sufficient oxygen supply. A further fundamental difference is that in the living body blood flows through a network of vessels having elastic walls with flow speeds which vary strongly in the rhythm of the blood pulse, while the liquid in a separating module flows at constant speed between rigid walls.

Evidently, it is not possible to derive from publications about the flow behavior in blood capillaries an indication that and how a practically useful separating module can be produced. Of special significance for the practical success of the invention is a preferred embodiment according to which the depth of the feed channel, preferably also the depth of the first drain channel and especially preferable the depth of all flow channels, is larger than the width, at least in the channel section directly adjoining the junction. This preferred embodiment relates to the fact that the separation of the particles is essentially determined by the width of the channels in the immediate neighborhood of the junction. By a depth which is large in relationship to the width, the separating performance (liquid volume separated per unit time) may be improved without impairing the function.

The invention will be described in greater detail here-after on the basis of exemplary embodiments shown in the figures. The features and elements shown and described may be used individually or in combination to provide preferred embodiments of the invention. In the figures:

DETAILED DESCRIPTION OF EMBODIMENTS OF THE PRESENT INVENTION

Figure 1:
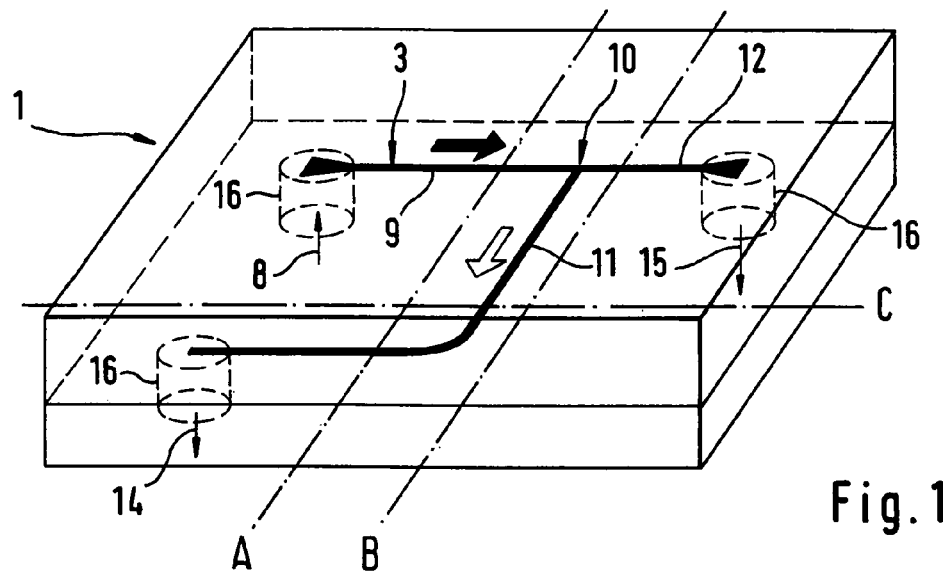
FIG. 1 shows a schematic perspective illustration of a first embodiment of a separating module according to the invention.

The separating module 1 shown in FIGS. 1 to 4 essentially comprises a channel part 2 having flow channels 3 and a cover part 4. During production of the channel part 2, the flow channels 3 are generated in a disk-shaped substrate 5, e.g. using one of the above-mentioned methods, forming microscopically small groove-shaped recesses in a surface 6 of the substrate 5.

Figure 2:
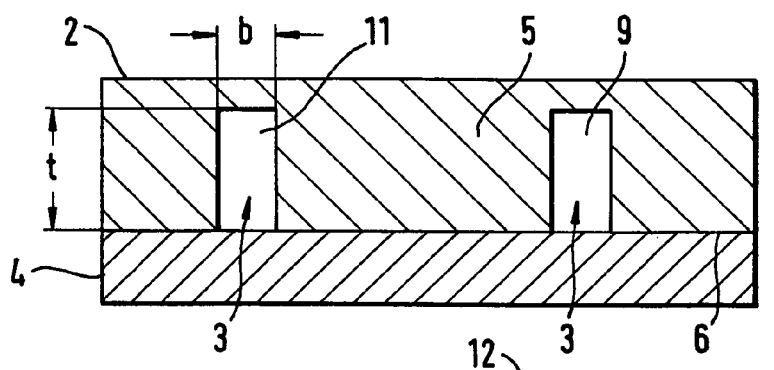
FIGS. 2-4 show cross-sectional illustrations (not to scale) along section lines A through C of FIG. 1.
Figure 3:
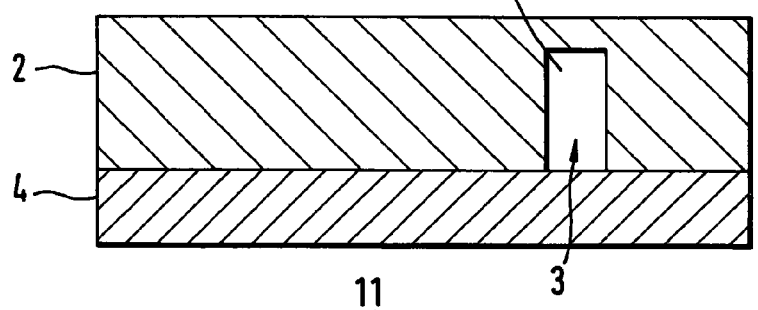
Figure 4:
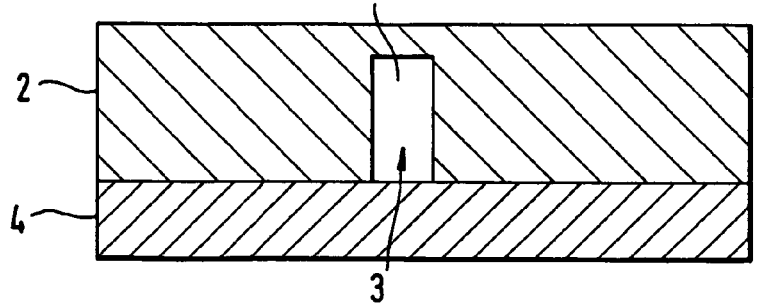

The channels are shown in a greatly exaggerated size, in particular in FIGS. 2 and 4. Typically, their width b is less than 150 μm. Channel widths of less than 100 μm, preferably less than 50 μm, have been found to be particularly suitable for obtaining plasma. However, the preferred dimensions are so much larger than the wavelength range of visible light that the necessary structures in the surface 6 of the substrate 5 can easily be generated by photolithographic methods, as are known from the production of electronic chips. The width b of the channels is preferably at least approximately 5 μm.

Whole blood (or another dispersion from which particles are to be separated) is fed into the separating module 1 via an inlet 8 and supplied to a junction 10 via a feed channel 9, at which the liquid flow divides into a first drain channel 11 and a second drain channel 12. The liquid flowing into drain channels 11 and 12 is removed from the separating module 1 via outlets 14 and/or 15. In the case shown, the inlets and outlets are formed by holes 16 provided in the cover part 4, to which suitable lines, such as plastic tubing, may be attached.

It is essential for the invention that the liquid flows so much faster in the second drain channel 12 than in the first drain channel 11 that due to the different flow speeds the dispersed particles preferentially flow at the junction 10 further in the second drain channel.

In the case of the treatment of blood, the first drain channel 11 contains plasma having a more or less small residual concentration of blood corpuscles (as a function of the processing conditions). It is therefore referred to hereafter as the plasma channel. The second channel 12 (having the higher flow speed) contains a higher concentration of blood corpuscles in comparison to the starting blood. Since this liquid is not used for analytical purposes, this channel-is hereafter designated the waste channel. However, these abbreviated terms may not be understood as a restriction of the field of application of the invention.

On the one hand, the "plasma channel" does not have to contain pure plasma. During the testing of the invention, it was determined that a single junction may be sufficient to obtain "analytical plasma", which is sufficiently pure for analytical purposes. However, the liquid flowing in the first flow channel typically contains a small residual concentration of blood corpuscles.

On the other hand, there are fields of application of the invention in which the purpose of particle separation is not (as in obtaining plasma) the purification of the carrier liquid of the dispersion, but rather the goal is to produce a concentrate of the dispersed particles. In this case, the first drain channel having the higher flow speed (which forms the waste channel in the case of obtaining plasma) does not contain waste, but rather the desired product.

The flow speeds in drain channels 11 and 12, their relation to one another, and the separating effect resulting therefrom is determined by a plurality of influencing factors, which may be divided into the following groups:

a) Flow resistance

If all other influencing factors for both drain channels 11, 12 are equal, the average flow rate is inversely proportional to the flow resistance of the channels.

b) Pressure ratios at the inlets and outlets

The pressure at the inlet 8 influences the flow speeds in the drain channels 11, 12 (assuming identical pressure ratios at the outlets 14, 15) essentially proportionally, thus not changing their relationship to one another. In contrast, differing pressure ratios at the outlets may have a large influence on the relationship of the flow speeds.

If in a specific application it is technically possible and economically feasible to connect a pump having an exact pump rate to at least one of the outlets 14, 15, the flow speed in the drain channels 11, 12 may be set via this pump rate. In the case of miniaturized analysis elements, the connection of a pump is typically not possible or at least too complex. In this case, however, the pressure ratios at the outlets 14, 15 may be influenced by suitable materials located there. Such materials may suck up the liquid by capillary forces and thus accelerate the flow in the preceding flow channel or they may form an additional flow resistance and thus reduce the flow speed.

c) Viscosity of the liquid

If the viscosity is different in the flow channels, the flow speed is influenced hereby. For example, in the case of obtaining plasma, the viscosity of the liquid is lower in the plasma channel 11 than in the waste channel 12. Assuming otherwise identical conditions this leads to a relative increase of the flow speed in the plasma channel 11.

d) Speed profile over the channel cross-section

The decisive factor for the separating effect is not the average flow speed of the liquid in the flow channel (volume flow per cross-sectional area and per time unit), but rather the local speed profile in the region of the junction. This again depends in a complicated way on various influencing factors, including the precise channel geometry, the material of the channel walls, and the viscosity of the liquid.

Because of this large variety of influencing variables, it is not possible to specify a rule for the dimensioning of the flow channels 3 which can generally be used for all application cases. The dimensioning must be experimentally determined in the individual case. Nonetheless, the following statements about advantageous dimensioning rules may be made on the basis of the experimental testing of the invention:

As already noted, the depths t of channels 9, 11, 12 are, at least in the channel sections directly adjoining the junction 10, larger than their width b. The aspect ratio A (ratio of the channel depth t to the channel width b: A=t/b) is preferably at least A=3, more preferably at least A=5, especially preferably at least A=7. Especially preferred is an embodiment in which the depths of at least the feed channel 9 and the plasma channel 11 are equal in the respective channel sections directly adjoining the junction 10. In a most preferred embodiment this is true for all channels 9, 11, 12 connected to the junction.

As has also already been noted, the smallest cross-sectional dimension of the plasma channel is at least 5 μm and at most 150 μm, values smaller than 100 μm, in particular smaller than 50 μm, being especially preferred.

The flow resistance of the plasma channel 11 should typically be higher than the flow resistance of the waste channel 12. This is preferably at least partially caused by making the plasma channel longer than the waste channel. This is advantageous because the flow resistance of the drain channels 11, 12 may be adjusted more easily and more precisely by a corresponding adjustment of their length than by a corresponding adjustment of the cross-section dimensions.

Furthermore, it is advantageous in regard to simple production and precise functioning if the depth t of the drain channels 11, 12 is equal for at least a part of their length, preferably for their entire length. The depth of the feed channel 9 preferably also is the same as the (equal) depth of the flow channels 11, 12.

The flow channels 3 have preferably a constant width over nearly their entire length. It has, however, been found to be advantageous if at least the feed channel 9 and the waste channel 12 are designed in the region of the inlet 8 and/or the outlets 15 in such a way that sharp corners, by which the erythrocytes may be damaged, are avoided. In this region a slanted shape of the walls of said channels 9 and 12 is indicated in FIG. 1.

For a simple production, it is favorable if at least the two drain channels 11, 12, and preferably also the feed channel, are equally wide.

Figure 5:
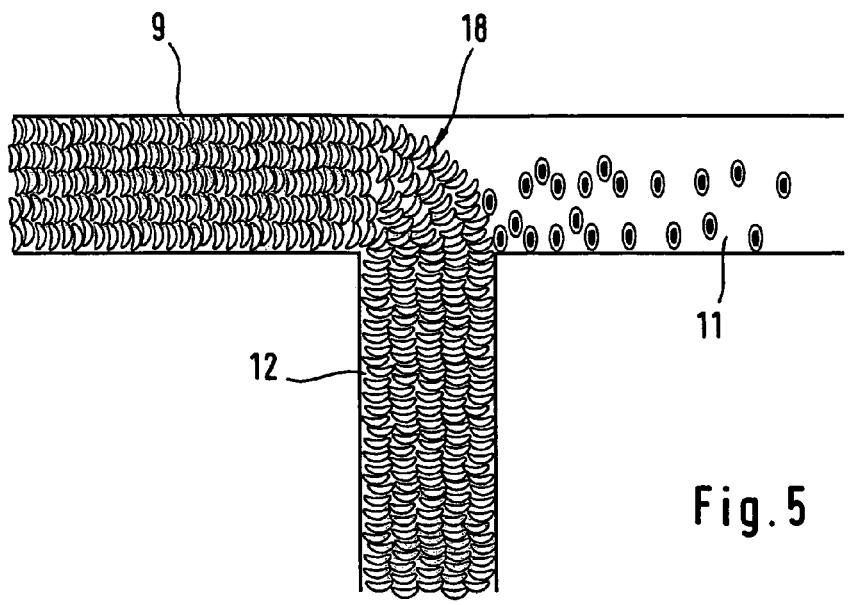
FIG. 5 shows a schematic drawing illustrating the separation effect visually observable at a junction by means of video equipment.

During experimental testing of the invention, the flow behavior of erythrocytes was observed with the aid of a microscope and video recorder directed at the junction. A schematic illustration of a typical image is shown in FIG. 5. Deviating from the separating module shown in FIGS. 1 to 4, in this case an arrangement was selected in which the plasma channel 11 continues straight in the direction of the feed channel 9, while the waste channel branches off at a right angle from this line. The illustration shows that the effect upon which the invention is based is essentially independent of the direction in which the drain channels 11, 12 branch off from the feed channel 9. The by far major share of the erythrocytes 18 follow the flow path having the larger flow speed, although in this case they must change their flow direction.

Figure 6:
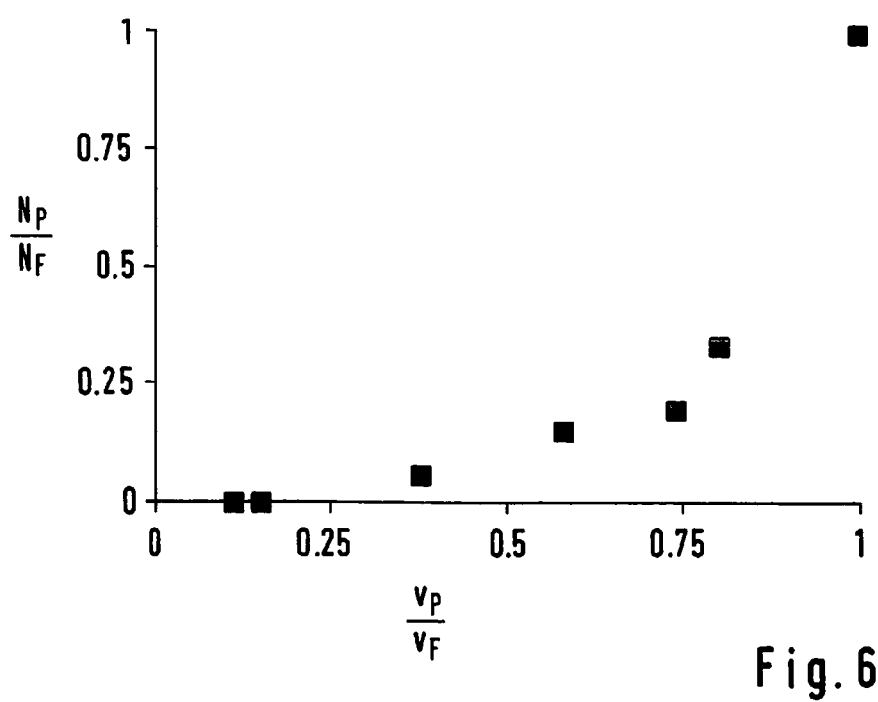
FIG. 6 shows a graph of the dependence of the separating effect on the relationship of the local flow speeds in the drain channels.

FIG. 6 shows a graph of experimental data which illustrates the dependence of the separating effect on the relationship of the flow speeds in the drain channels. It was obtained using a separating module corresponding to FIG. 1, the feed channel 9 and the waste channel 12 each being 32 μm wide and 32 μm deep. The plasma channel 11 was 16 μm wide and 32 μm deep. The flow per unit time in the feed channel 9 was in the range between 0.01 and 0.5 μl/minute. The relationship of the flow speed $v_P$ in the plasma channel 11 to the flow speed $v_F$ in the feed channel are plotted on the abscissa. The ordinate shows the corresponding relationship of the particle counts $N_P$ to $N_F$. The experiments were performed using blood diluted in the ratio 1:5 in order to make the erythrocytes more recognizable. The speeds $v_P$ and $v_F$ were derived from the video observation of the erythrocytes flowing in the central flow path. The particle counts were also determined from the video data.

It may be seen that the separating effect rapidly becomes better when the speed ratio $v_P/v_F$ goes down. At a speed ratio of 0.75, approximately 25% of the original erythrocyte count still flows in the plasma channel. When the flow speed in the plasma channel is less than one-fourth of the flow speed in the feed channel, excellent purity of the plasma in the plasma channel is achieved.

Figure 7:
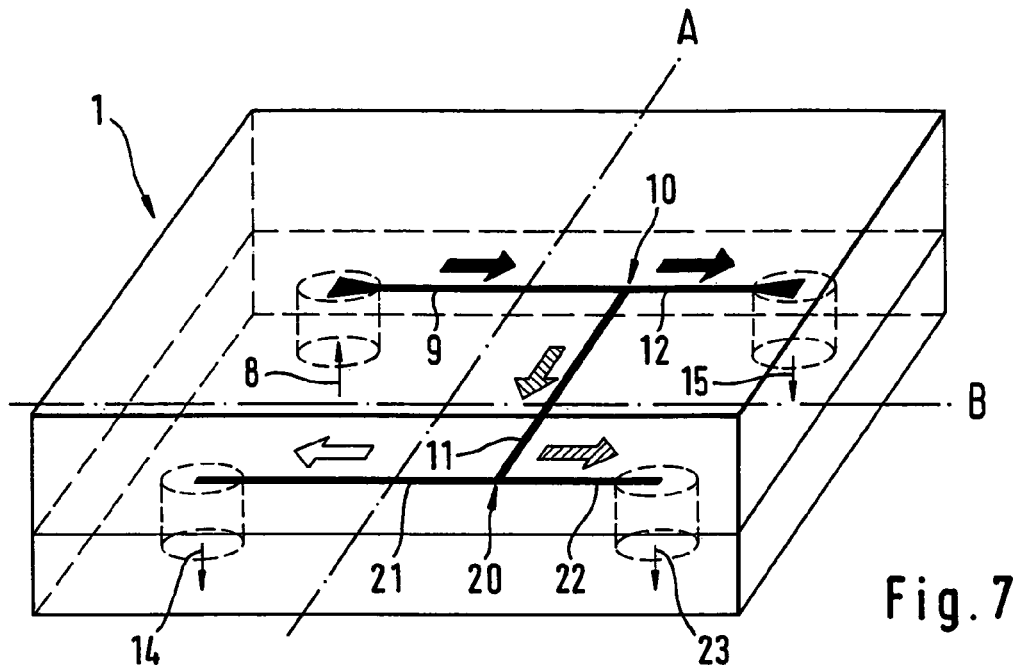
FIG. 7 shows a schematic perspective illustration of a second embodiment of a separating module according to the invention.
Figure 8:
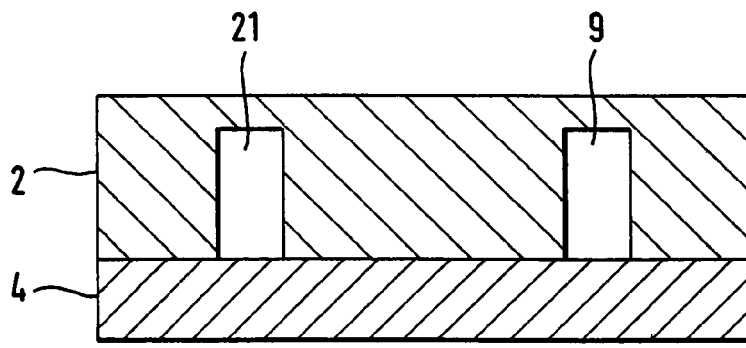
FIGS. 8 and 9 show cross-sectional illustrations (not to scale) along section lines A and B of FIG. 7.
Figure 9:
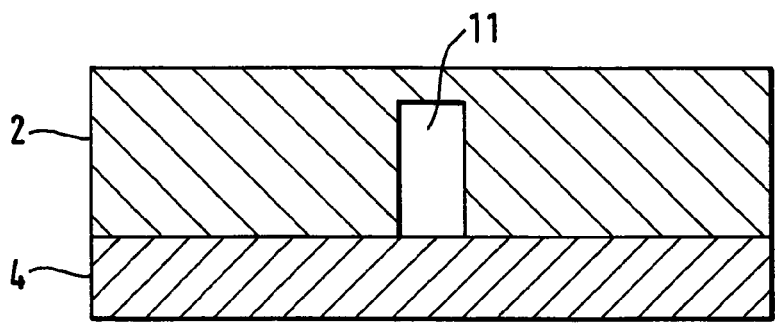

FIGS. 7 through 9 show an embodiment of a separating module in which two junctions 10 and 20 are positioned one behind another in the flow channels leading from the inlet 8 to the plasma outlet 14 in such a way that the overall separating effect is improved by a two-stage separating process. This may be achieved in that—as shown—the plasma channel originating from the first junction 10 leads to a further junction 20 in such a way that it forms a feed channel for the further junction 20 and a further plasma channel 21 and a further waste channel 22 branch off from the further junction 20, the plasma channel 21 leading to the plasma outlet 14 and the waste channel 22 leading to a second waste outlet 23. The dimensions of the drain channels and the operating conditions are again selected in such a way that the liquid in the further waste channel 22 flows so much faster than in the further plasma channel 21 that a separation into a liquid flow having a higher particle concentration (waste channel 22) and a liquid flow having a lower particle concentration (plasma channel 21) occurs at the second junction 20.

If even the purity of the plasma achievable by a two-stage separating process is not sufficient, the separating method may also be performed in three stages or a plurality of stages using a correspondingly altered separating module. A separating module suitable for this purpose (not shown) has a sequence of junctions, each of whose feed channel is formed by the plasma channel of the preceding junction, the flow speed ratios described being maintained at each of these junctions.

Figure 10:
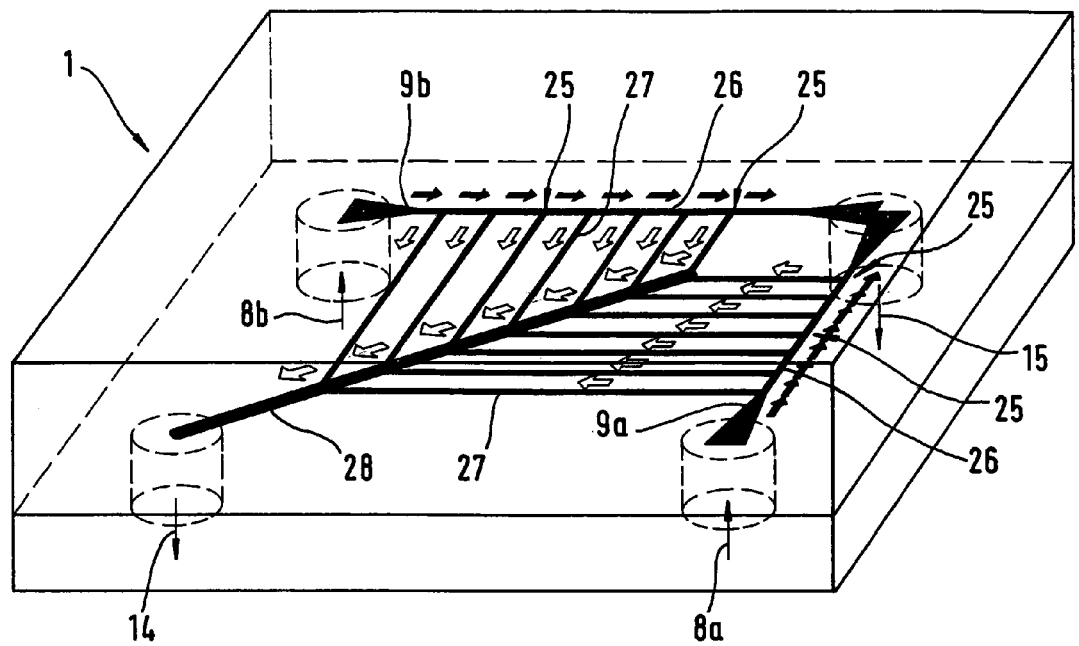
FIG. 10 shows a perspective illustration (not to scale) of a third embodiment of a separating module according to the invention.

FIG. 10 shows an embodiment of a separating module 1 in which an increased separating performance is achieved by a sequence of junctions 25 positioned one behind another in such a way that each of the waste channels of the preceding junction forms the feed channel of the subsequent junction. The plasma channels 27 branching off from the junctions 25 lead to a common collection line 28 and from there to the plasma outlet 14. In the case shown, this arrangement is provided symmetrically twice, the blood being fed through inlets 8a and 8b into the first feed channel 9a and 9b, respectively. From there, it flows along a channel 26a and 26b, respectively. The sections of these tunnels which lye between the junctions 25 each form the waste channel of the preceding junction and the feed channel of the subsequent junction. The separating effect according to the invention causes a continuous increase of concentration of the erythrocytes in these channels 26a and 26b. In order to nonetheless achieve a uniform plasma quality, the plasma channels are dimensioned (in the case shown with respect to their length) in such a way that the flow speed of the liquid transported therein is reduced in the direction in which the erythrocyte concentration supplied to the particular junction increases.

Figure 11:
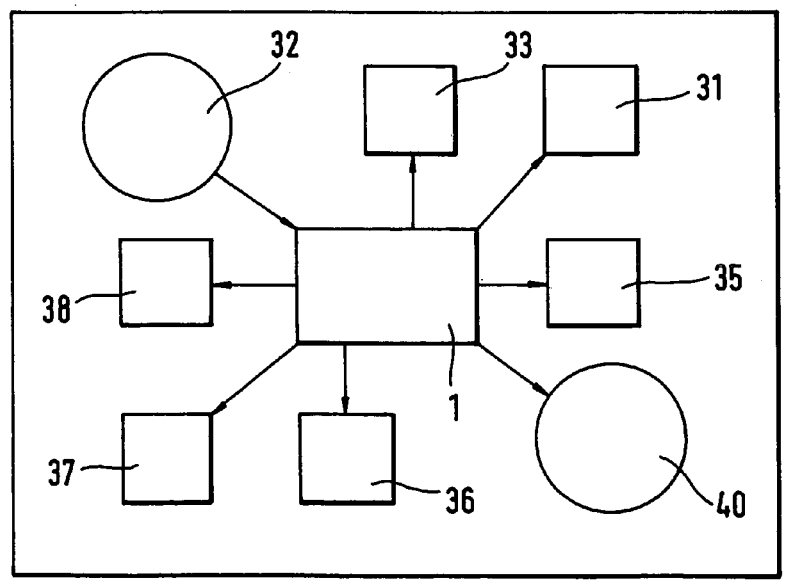
FIG. 11 shows a schematic top view of an analysis element with planar integration of a separating module according to the invention.

FIG. 11 shows a possible conception, according to which a separating module 1 is integrated in planar form into an analysis chip 31, together with other modular elements necessary for an analysis. In this case, the inlet of the separating module 1 is connected to a blood reservoir 32. Test modules 33 through 38 are connected to a plurality of outlets of the separating module 1, which may be used for determining different analytes or for more precise analysis of different concentration ranges of the same analyte, for example. Finally, a waste container 40 is integrated into the analysis chip 31, into which the liquid from one or more waste outlets of the separating module 1 is conducted.

As noted, reference was made in the preceding descriptions to the separation of blood corpuscles from blood to obtain plasma solely for exemplary purposes and without restriction of the general applicability of the invention. The explanations accordingly apply equally for other applications. In this case, the term "plasma channel" has to be replaced by "first channel", the term "waste channel" by "second channel", the term "waste" by "liquid having increased particle concentration", and the term "plasma" by "liquid having reduced particle concentration".

The invention claimed is:

1. A method for separating particles from a fluid dispersion, particularly for separating corpuscular components from biological samples; the method comprising:
providing a separating module comprising a substrate with flow channels forming groove-shaped recesses in a surface of the substrate;
supplying the fluid dispersion to a junction through a feed channel;
draining the fluid dispersion having a reduced particle concentration away from the junction through a first drain channel;
draining the fluid dispersion having an increased particle concentration away from the junction through a second drain channel; and
wherein the fluid flow is much faster in the second drain channel than in the first drain channel such that due to the different flow speeds, the dispersed particles at the junction preferentially flow further in the second drain channel.

2. The method according to claim 1, in which the first drain channel leads to a further junction, so that it forms a feed channel for the further junction and a further first drain channel fur draining fluid having a reduced particle concentration and a further second drain channel for draining fluid having an increased particle concentration branch off from the further junction, wherein the fluid flows so touch faster in the further second drain channel than in the further first drain channel that due to the different flow speeds the dispersed particles preferentially flow at the further junction into the further second drain channel.

3. The method according to claim 2, wherein funning a sequence of junctions, each having a feed channel formed by the first drain channel of the preceding junction, wherein the fluid flows so much faster in the particular second drain channel originating from a junction than in the particular first drain channel originating from the junction that due to the different flow speeds the dispersed particles flow at each of the junctions further in the particular second drain channel.

4. The method according to claim 1, wherein the second drain channel leads to a further junction, so that it forms a feed channel for the further junction, and a further first drain channel branches off from the further junction for draining fluid having a reduced particle concentration, and a further second drain channel branches off from the further junction for draining fluid having an increased particle concentration, wherein the fluid flows so much faster in the further second drain channel than in the further first drain channel that due to the different flow speeds the dispersed particles preferentially flow at the further junction further in the further second drain channel.

5. The method for separating particle according to claim 4 by means of a separating module which has a sequence of junctions, each having a feed channels formed by the second drain channel of the preceding junction, wherein the fluid flows so much faster in the particular second drain channel originating from a junction than in the particular first drain channel originating from the junction that due to the different flow speeds the particles dispersed in the fluid preferentially flow at each of the branches farther in the particular second drain channel.

* * * * *